(12) United States Patent
Orejola (10) Patent No.: US 8,579,788 B2
(45) Date of Patent: Nov. 12, 2013

(54) AUTO-REGULATED R-WAVE SYNCHRONIZED INTRAVENTRICULAR BALLOON PUMP HEART ASSIST DEVICE

(76) Inventor: Wilmo Orejola, Pompton Plains, NJ (US)

( * ) Notice: Subject to any disclaimer, the term of this patent is extended or adjusted under 35 U.S.C. 154(b) by 919 days.

(21) Appl. No.: 12/719,139

(22) Filed: Mar. 8, 2010

(65) Prior Publication Data

US 2011/0218382 A1 Sep. 8, 2011

(51) Int. Cl.
*A61M 1/12* (2006.01)

(52) U.S. Cl.
USPC .......................................................... 600/16

(58) Field of Classification Search
USPC .................. 600/16; 623/3.16–3.18, 3.21–3.23
See application file for complete search history.

(56) References Cited

U.S. PATENT DOCUMENTS

| | | |
|---|---|---|
| 4,861,330 A | 8/1989 | Voss |
| 4,902,273 A | 2/1990 | Choy et al. |
| 5,092,879 A | 3/1992 | Jarvik |
| 5,139,517 A | 8/1992 | Corral |
| 5,147,388 A | 9/1992 | Yamazaki |
| 5,776,190 A | 7/1998 | Jarvik |
| 5,888,241 A | 3/1999 | Jarvik |
| 5,910,124 A | 6/1999 | Rubin |
| 6,245,007 B1 | 6/2001 | Bedingham et al. |
| 6,511,413 B2 | 1/2003 | Landesberg |
| 6,610,004 B2 | 8/2003 | Viole et al. |
| 7,361,137 B2 | 4/2008 | Taylor et al. |

*Primary Examiner* — Christopher D Koharski
*Assistant Examiner* — Jeremiah Kimball
(74) *Attorney, Agent, or Firm* — Michael J. Feigin, Esq.; Feigin & Associates, LLC (57) ABSTRACT

Embodiments of the disclosed technology comprise an intraventricular balloon pump to help a dilated heart or ventricle push forward the stagnant stroke volume to the systemic circulation. The balloon fills simultaneously with the contraction of the ventricle. Since blood finds its way of least resistance, the easiest exit is through the aortic valve, against a closed mitral valve. The system is designed to be totally implantable, with a less invasive insertion and maintenance procedure than is known in the prior art.

20 Claims, 7 Drawing Sheets

Figure 13

AUTO-REGULATED R-WAVE SYNCHRONIZED INTRAVENTRICULAR BALLOON PUMP HEART ASSIST DEVICE

FIELD OF THE DISCLOSED TECHNOLOGY

The disclosed technology relates generally to heart balloon pumps and more particularly to such pumps inserted into the left ventricle.

BACKGROUND OF THE DISCLOSED TECHNOLOGY

There are approximately five million Americans suffering from heart failure. About 550,000 new cases are diagnosed every year and, at any given time, there are nearly a half million Americans living with advanced stage heart failure (e.g., stage III or stage IV heart failure). Approximately 280,000 people die from heart failure each year in the United States.

In heart failure, the left ventricle does not adequately contract to force the blood volume to the systemic circulation. Only a fraction of this volume (usually less than 35%) is ejected, which means that the rest of the volume remains in the ventricle causing it to dilate improperly. Starling's law of the heart states that the greater the volume of blood entering the heart during diastole (end-diastolic volume), the greater the volume of blood ejected during systole (stroke volume). Like a rubber band, the further the heart is stretched the greater is the recoil. However, this works only up to a certain point. When the heart muscles are weakened from infarction or infection, wall tension of the heart does not allow it to expand further to accommodate increase in its radius (Law of Laplace), which explains heart failure.

While heart failure can be treated medically in most cases, once the problem has reached advanced stages, medication becomes less or not at all effective. Medical devices have been used safely and effectively to assist the failing heart and the circulation. There are many assist devices already available, including total artificial hearts (TAH) and ventricular assist devices (VADs). However, in about a third of failing hearts with these devices, total recovery is achieved only by patients who are 40 years old or younger, with a non-ischemic heart as the cause of failure, and, even then, a full recovery is only possible within the first six months. The rest of such patients typically need a heart transplant to survive. Some 60,000 end-stage heart failure patients in the United States need such heart transplants, but only about 2,100 are available every year. VADs and TAH will continue to play a role as temporary circulatory support, as will bridge-to-heart transplantation or destination therapy, due to the shortage of organs available for use as transplants.

There are various forms of VADs, driven by either pulsatile or continuous rotary pumps. Although approved for clinical uses, presently available designs are still prone to serious complications such as infection, bleeding and stroke. No device has been designed that would obviate the need for anticoagulation, which is essential for these devices. Excessive anticoagulation causes bleeding while inadequate anticoagulation can lead to strokes. While medical technology has progressed with the use in the past fifty years of Intra-aortic Balloon Pumps (IABP), aside from indirectly improving remaining heart function by increasing coronary perfusion during diastole and reducing afterload during systole, it has also proven that anticoagulation may not be necessary during circulatory support where interface between patient and device is limited.

SUMMARY OF THE DISCLOSED TECHNOLOGY

Embodiments of the disclosed technology include an Intraventricular Balloon (IVB) pump introduced through the left ventricular apex, which helps a failing heart by improving stroke volume and lowering end-diastolic volume. The IVB of the disclosed technology allows the heart to rely on natural valves and conduits, without the need for artificial heart valves and conduits that are integral to many VAD designs. Thus, anticoagulation may not be indicated. The partial heart support allows the heart to continue to be active and regain more strength compared with a heart which is totally supported by artificial means, and, thus, the present technology is directed towards assisting a failing heart or providing some "rest" while a heart is recovering.

The technology disclosed is a left ventricular assist device which functions via volume displacement. A volume of hydraulic medium in a pulsatile closed system inserted into the left ventricle through the apex displaces equal amounts of blood out of the ventricle to the systemic circulation. The technology is used with the naturally occurring valves and arteries found in the heart. The technology is implantable and includes a rotating disc assembly that is automatically triggered by heart contractions and powered by a battery. In an embodiment thereof, the battery is charged via a transcutaneous energy transmission (TET) and lacks exterior cabling.

In a method of using the device of the disclosed technology, the IVB pump is activated only upon a myocardial contraction or R-wave sensing. If there is no myocardial contraction or R-wave sensing, the IVB pump is not activated. In case of arrhythmias, the pump will not work against blood flow. However, when the heart is arrested, in an embodiment of the method of the disclosed technology, the IVB pump is converted to a continuous mode in order to internally take-over cardiac resuscitation, e.g., it is a form of internal cardiac massage.

A system of the disclosed technology is an intraventricular balloon pump system with an intraventricular balloon, a housing comprising a rotating disc and a tubule, the tubule fluidly connected with said balloon. A revolution of the rotating disc compresses the tubule and forces fluid held within the tubule to enter the balloon. This is timed with the beating of a heart (R-wave synched) in embodiments of the disclosed technology. An electrical contact timed with an R-wave electrical signal/contraction of the heart causes the rotating disc to turn in such embodiments.

A method of ventricular assist of a heart includes filling a tubule with liquid, the tubule extending into a circular housing, detecting a myocardial contraction, and upon detecting the contraction, such as with a switch mounted on the outside of a heart, rotating a quadrant about a central axis of the circular housing so as to sweep the liquid out of the circular housing into an intraventricular balloon. When the heart beats regularly, the quadrant alternates between movement and rest, as needed, but during a cardiac arrest, the quadrant spins continuously as a form of internal heart massage, in embodiments of the disclosed technology.

An access port in fluid connection with said tubule and the balloon is further provided in embodiments of the disclosed technology, so as to allow for decreasing or increasing the fluid volume when less or more heart assist is needed, such as up to the volume of the left ventricle.

DETAILED DESCRIPTION OF EMBODIMENTS OF THE DISCLOSED TECHNOLOGY

Embodiments of the disclosed technology comprise an intraventricular balloon pump to help a dilated heart or ventricle push forward the stagnant stroke volume to the systemic circulation. The balloon fills simultaneously with the contraction of the ventricle. Since blood finds its way of least resistance, the easiest exit is through the aortic valve, against a closed mitral valve. The system is designed to be totally implantable, with a less invasive insertion and maintenance procedure than is known in the prior art.

A system of the disclosed technology is an intraventricular balloon pump system with an intraventricular balloon, a housing comprising a rotating disc and a tubule, the tubule fluidly connected with said balloon. A revolution of the rotating disc compresses the tubule and forces fluid held within the tubule to enter the balloon. This is timed with the beating of a heart (R-wave synched) in embodiments of the disclosed technology. An electrical contact timed with an R-wave electrical signal/contraction of the heart causes the rotating disc to turn in such embodiments.

A method of ventricular assist of a heart includes filling a tubule with liquid, the tubule extending into a circular housing, detecting a myocardial contraction, and upon detecting the contraction, such as with a switch mounted on the outside of a heart, rotating a quadrant about a central axis of the circular housing so as to sweep the liquid out of the circular housing into an intraventricular balloon. When the heart beats regularly, the quadrant alternates between movement and rest, as needed, but during a cardiac arrest, the quadrant spins continuously as a form of internal heart massage, in embodiments of the disclosed technology.

Embodiments of the disclosed technology will become clearer in view of the foregoing description of the Figures.

Figure 1:
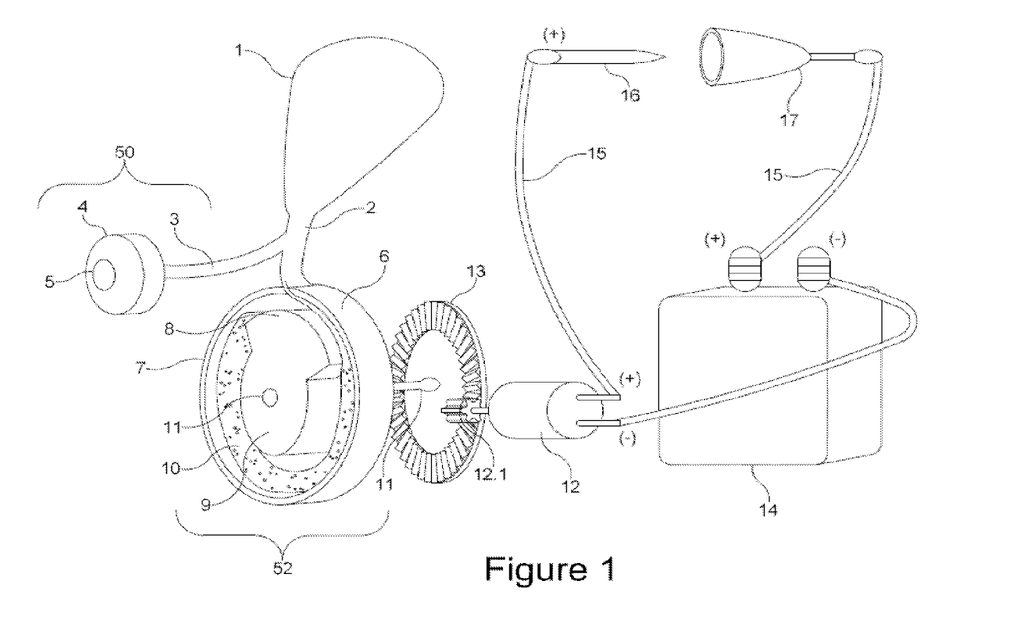
FIG. 1 shows a high level drawing of the device of the disclosed technology in an embodiment of the disclosed technology.

FIG. 1 shows a high level drawing of the device of the disclosed technology in an embodiment of the disclosed technology. The device includes an intraventricular balloon (IVB) 1, R-wave-synchronizer switch comprising a spindle 16 and receptacle 17, hydraulic (or pneumatic) access port 50 comprising a stem 2, conduit 3, and fluid reservoir 4, rechargeable battery 14, motor-rotating disc-tubule assembly 52 comprising a housing 7, tubule 6, protruding quadrant 8, rotating disc 9, and reservoir 10, and a gate mechanism 11 between the motor-rotating disc-tubule assembly 52 and motor 12 with gear shaft 12.1. The battery 14 is electrically connected to the receptacle 17 of the switch and the motor 12. The motor is further electrically connected to the spindle 16 of the switch and is implanted subcutaneously. Regular recharging of the battery is done through transcutaneous energy transmission (TET).

As will be shown and described in more detail with reference to later figures, as the heart beats, the parts of the switch 16 and 17 become electrically engaged, powering the motor in such a manner as to be synchronized with the beating of the heart. A gear shaft 12.1 of the motor assembly is gearedly engaged with a gear 13 of the motor-rotating disc-tubule assembly, which is, in turn, gearedly engaged with the rotating disc 9, which is, in turn, engaged with, or forms, a unitary structure with a rotating quadrant 8. As the quadrant rotates, a reservoir 10 (the reservoir being contained in the housing 7 near the circumferential exterior of the circular border thereof,) is swept through by the protruding quadrant 8. In this manner, the liquid (shown in black in FIG. 1) is pulled up into the balloon with each heart beat. The balloon 1, in embodiments of the disclosed technology, is inserted through the apex and into the left ventricle of the heart and assists a failing heart.

Referring now to the access port 50, the access port is comprised of, or consists of, a conduit 3 and the fluid reservoir 4. By way of the access port, fluid may be introduced into the device before, during, or after implantation of the device. In an embodiment of the disclosed technology, chamber 4 has a round opening covered with rubber diaphragm 5. The stem 2 of the IVB is fluidly attached to the conduit 3 and is further fluidly engaged with the tubule 6 which circles the outer portion of the interior of the housing 7. The tubule 6 curls in front of, and near the circumference of, rotating disc 9. The reservoir gap 10, between the rotating disc 9 and around the quadrant 8 in housing 7, serves as a moving reservoir for fluid medium. The protruding quadrant 8 of the rotating disc 9 sweeps the fluid medium from the tubule 6 to the balloon 1.

The reservoir 4, in embodiments of the disclosed technology, is a hollow flat metallic cylinder that has a small round opening covered by a rubber diaphragm or port. The access port is implanted subcutaneously. Hydraulic (saline solution) or pneumatic (carbon dioxide) medium is injected or withdrawn into or out of this access port, in embodiments of the disclosed technology.

Figures 2, 3:
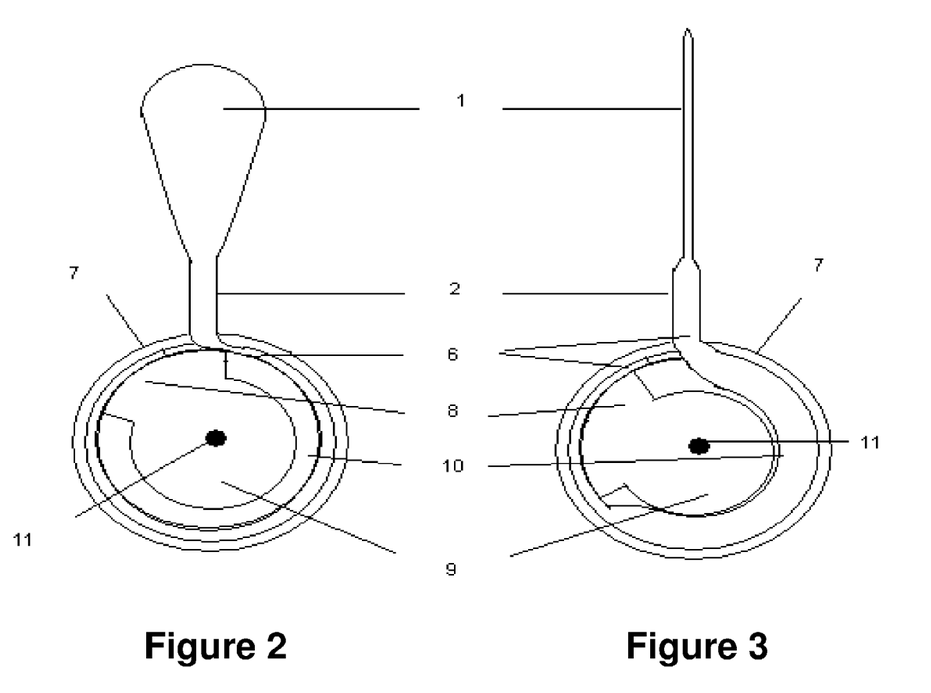
FIG. 2 shows a position of a protruding quadrant and balloon just after systole in an embodiment of the disclosed technology.
FIG. 3 shows a position of a protruding quadrant and balloon just after diastole in an embodiment of the disclosed technology.

FIG. 2 shows a position of a protruding quadrant and balloon just after systole in an embodiment of the disclosed technology. FIG. 3 shows a position of a protruding quadrant and balloon just after diastole in an embodiment of the disclosed technology. Referring to FIGS. 2 and 3 in general, the housing 7 is situated beneath the IV balloon 1. That is, the balloon is inserted through the apex of the heart into the left ventricle, and the housing is beneath the heart/balloon 1 and is in fluid connection with the balloon by way of stem 2. At a first position, as shown in FIG. 3, the rotating disc with protruding quadrant 8 has moved past the opening in the housing 7 where the stem 2 enters and becomes the tubule 6. As such, gravity and diastole pull/push the fluid out of the balloon and into the tubule 6. The balloon is deflated.

Now referring to FIG. 2, in another position, just after systole, the balloon is fully inflated because the rotating quadrant 8 has swept the fluid out of the tubule 6, and the hollow interior space 10 of the housing 7 is substantially emptied (greater than 90% emptied) of liquid. In this position, due to the length of the portion of the rotating quadrant 8 of the rotating disc 9 which spins around axis 11, once the fluid has been pushed into the IVB 1, it remains there until the quadrant 8 passes the opening of the housing and allows the fluid to flow back into the tubing 6. It should be noted that a tubule 6 extends within the interior space or reservoir gap 10 of the housing 7, such that fluid passes to and from the stem only in one direction around the interior space, e.g., the tubule is an extension of the balloon 1 into the interior space of the housing 7. The rotating disc with quadrant 8 pushes fluid up the balloon and then allows it to fall back into the tubule 6.

Referring now to the IVB in more detail, the IVB, in an embodiment of the disclosed technology, is cone-shaped or generally elongated and may be procured from a polyurethane membrane. In embodiments of the disclosed technology, the IVB may form a unitary structure with the stem 2 through to the tubule 6. When emptying, the balloon collapses into a thin leaf-like sheet overlying the ventricular septum where it's free of papillary muscles. A pulse is generated by pumping the liquid medium, which may be a saline solution or carbon dioxide solution in and out of the IVB.

In an embodiment of the disclosed technology, the IVB is inserted as follows. A small incision is made over the pericardium through the fourth intercostal space. The pericardium is incised to get access to the apex of the left ventricle. Under trans-esophageal echocardiographic (TEE) or trans-thoracic echocardiographic (TTE) guidance, a needle is inserted into the apex of the left ventricle. A guide wire is passed into it. The needle is withdrawn leaving the guide wire. A dilator is passed over the guide wire. The introducer sheath is passed over the guide wire. The IVB is collapsed inside a plastic cover. It is inserted into the ventricle by way of an introducer sheath. The introducer sheath is withdrawn. Using an echocardiogram, the IVB is positioned properly at the ventricular septum, away from the anterior and posterior papillary muscles. Then, the stem of the IVB is secured at the apex with pledgeted prolene sutures. This stem conduit is connected to the end of the tubule in the pump housing. Initial test runs are done with various hemodynamic parameters. Timing and volume of the medium are adjusted. Pockets are created subcutaneously in the upper abdomen for the pump and motor, rechargeable battery and the port access. The chest incision is closed.

The filling of the intraventricular balloon 1 is synchronized with the R-wave of the electrocardiogram (ECG) or ventricular contraction (systole). Likewise, IVB emptying coincides with ventricular relaxation (diastole) and the negative pressure created by the collapsed balloon draws in blood from the left atrium to aid in filling the left ventricle. In a filled connection, such as during diastole, the balloon 1 may maximally fill the whole volume of the ventricle (defined as 95% or more of the interior space of the ventricle) and hold approximately 100 ml of liquid maximum. The filling volume, however, is adjustable according to the degree of assistance needed. The volume may be decreased or increased by way of adding or removing liquid through the access port 5, so as to regulate the degree of assistance according to the needs and volume of the ventricle. A fully filled balloon, i.e., 100 ml, at systole would become occlusive if the ventricle achieves a normal ejection fraction of 65%. Thus, IVB pumping is used only where, and to the extent that, the ejection fraction is below normal.

When no longer needed, the IVB pump can be removed as follows. When optimum hemodynamic parameters have been achieved, and it is deemed safe to discontinue ventricular assistance, the IVB pump system may be extracted. Incision is made at the site of the previous incision. The devices are disconnected and explanted. The previous pericardial incision is opened. The LV apex point of insertion of the IVB is exposed. Pledgeted polypropylene sutures are applied around the insertion site. The sutures are ensnared and tightened. The IVB is withdrawn gently from the ventricle. The sutures are tied to secure the heart from bleeding at the site. The chest incision is closed in layers.

Figure 4:
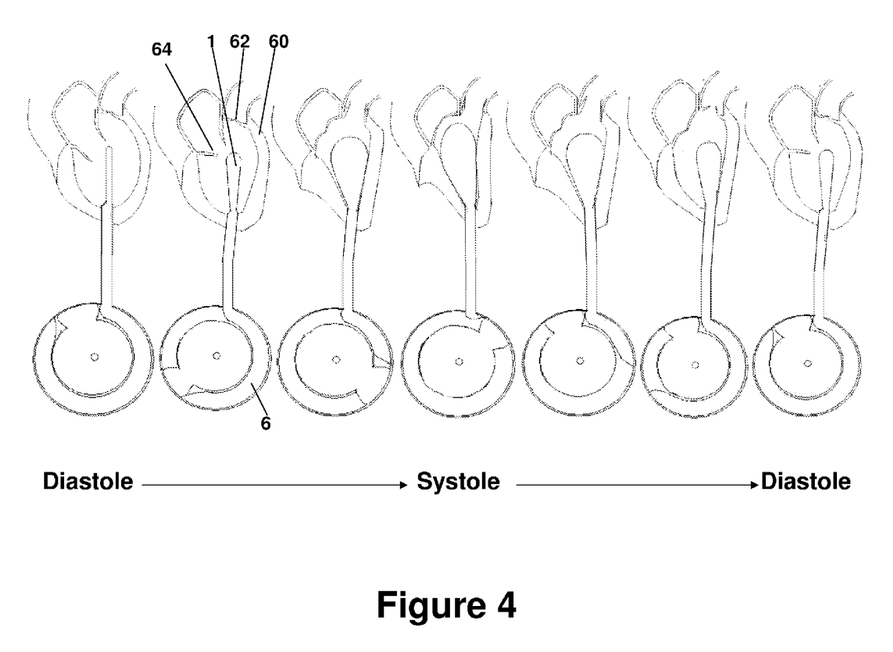
FIG. 4 shows six positions of a heart, IV balloon, and fluid within a housing during a cardiac cycle in an embodiment of the disclosed technology.

FIG. 4 shows six positions of a heart, IV balloon, and fluid within a housing during a cardiac cycle in an embodiment of the disclosed technology. Starting at the extreme left, during diastole, as the heart 60 is filling with blood, the IVB 1 is empty. The dilated IVB helps the weak heart pump more blood out of the aortic valve 62 to the circulation. Once reaching systole (fourth figure from the left), the portion of the balloon 1 within the left ventricle is filled and, as the R-wave hits as diastole begins with the relaxing of the heart, the rotating disc stops. It is timed such that it has moved past the opening from the housing 7 to stem 2, and the fluid in IVB 1 is pushed back/falls back into the tubule 6. During diastole B, IVB 1 is collapsed allowing more blood to fill into the ventricle through a wide open mitral valve 64. As shown in the right three drawings, the tubule fills up, and the cycle is ready to begin again, with a new sweeping of the disc, rotating in 360 degrees.

Figures 5, 6:
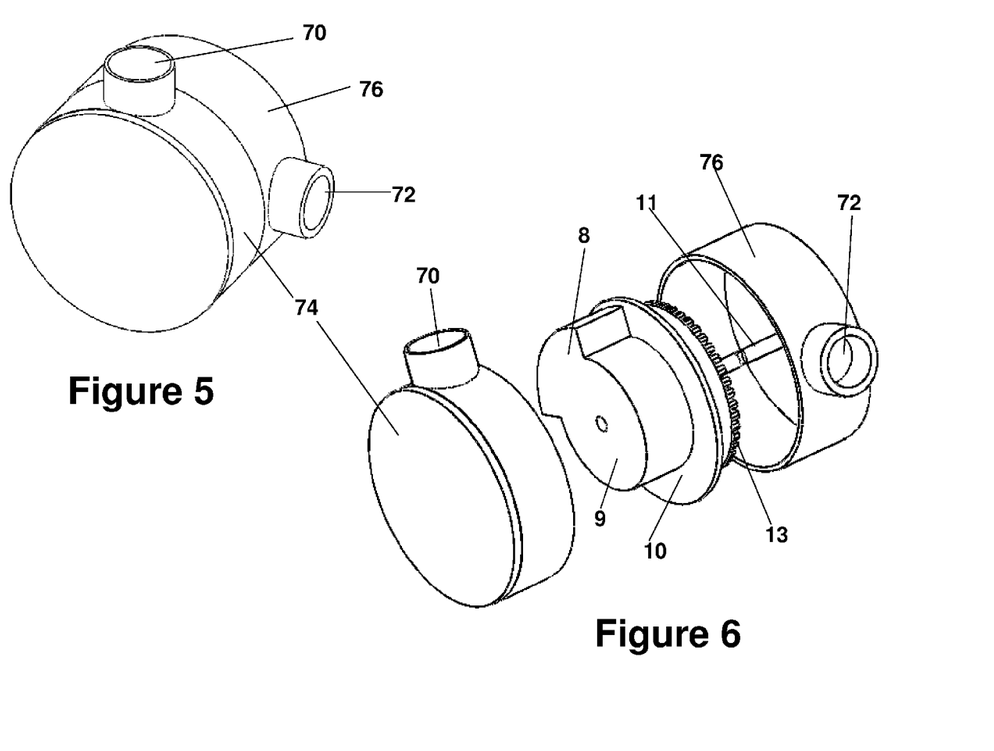
FIG. 5 shows a perspective view of an exterior portion of a housing with rotating disc in an embodiment of the disclosed technology.
FIG. 6 shows an exploded view of the housing with rotating disc in an embodiment of the disclosed technology.
Figures 10, 11:
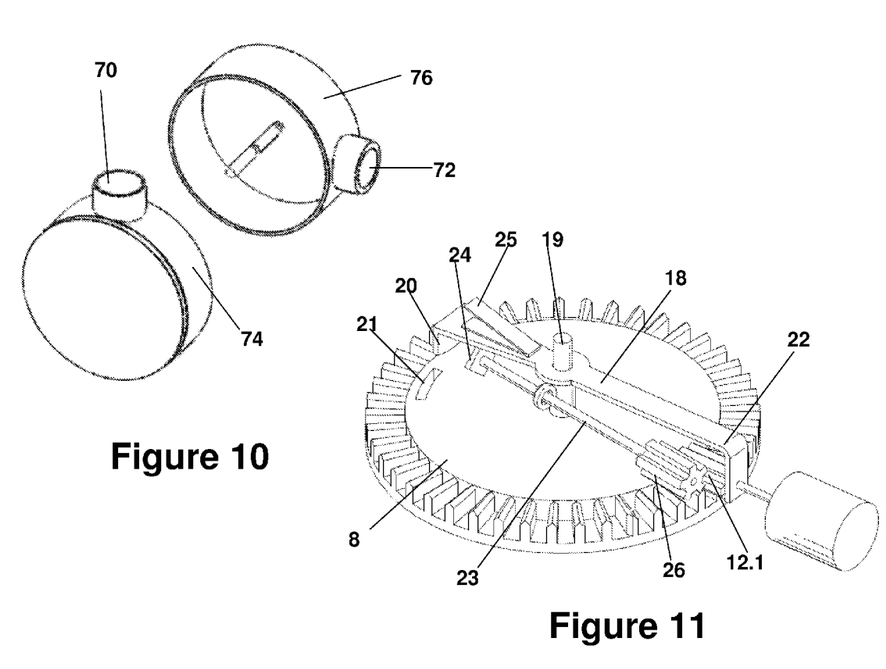
FIG. 10 shows an exploded view of the housing assembly of an embodiment of the disclosed technology.
FIG. 11 shows a gate mechanism within the housing in an embodiment of the disclosed technology.

FIG. 5 shows a perspective view of an exterior portion of a housing with rotating disc in an embodiment of the disclosed technology. FIG. 6 shows an exploded view of the housing with rotating disc in an embodiment of the disclosed technology. FIG. 10 shows an exploded view of the housing assembly of an embodiment of the disclosed technology. The housing (numbered 7 in FIG. 1) comprises an outlet 70 where a stem (numbered 2 in FIG. 1) which is fluidly connected to, and/or forms a unitary structure with, IVB 1 enters the housing or tubule 6 (of FIG. 1) into the housing cover 74. A second outlet 72 is adapted for entry of a shaft of a motor, such as motor 12 of FIG. 1. Referring now especially to FIG. 6, inside the housing is a beveled disc gear 13, or any other gear known in the art, which engages with a gear shaft of a motor (e.g., gear shaft 12.1, shown in FIG. 1). The disc gear 13 is fixedly connected to, or forms a unitary structure with, the rotating disc 9 and protruding quadrant 8, the quadrant covering a portion, such as less than 50%, 30%, or 25% of the circumference, of the rotating disc 9. The disc gear 13 and rotating disc 9 combination is held to the back side of the housing 76 by way of an axis 11, in the embodiment shown. In this manner, as the motor operates (synced to the R-wave of the heart beat), the protruding quadrant 8 makes a full revolution and pushes fluid from a tubule (numbered 6 in FIG. 1) out through the portal 70 and into the IVB. As the quadrant 8 passes the outlet 70, liquid falls out of the IVB and back through the stem and into the tubule 6, that is, to the space or reservoir gap 10 between the housing cover 74 and rotating disc 9.

Figures 7, 8, 9:
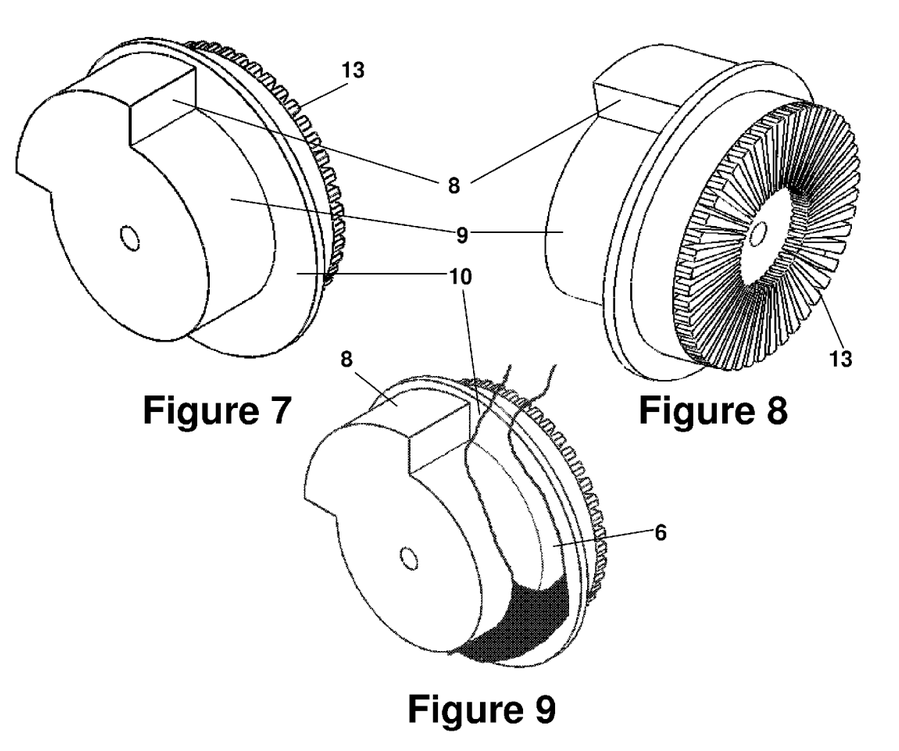
FIG. 7 shows a perspective view of a front side of a rotating disc comprising a protruding quadrant in an embodiment of the disclosed technology.
FIG. 8 shows a perspective view of a back side of a rotating disc, further comprising a gear engageable for turning the disc in an embodiment of the disclosed technology.
FIG. 9 shows a perspective view the front side of the rotating disc as shown in FIG. 7, with a tubule extending around the disc.

Referring still to FIGS. 5, 6 and 9, the motor-rotating disc-tubule assembly functions as follows. The tubule is a collapsible plastic hook-shaped tubing outlying the circumference of the rotating disc 9. It serves as reservoir for the fluid medium in the motor-rotating disc-tubule assembly. The rotating disc, in an embodiment of the disclosed technology, is between half an inch and two inches thick, such as one inch thick and may be procured from metal or hard plastic. As the disc turns counterclockwise or clockwise (a system of the disclosed technology would be designed to turn one way or the other), this protruding part sweeps the fluid medium in the tubule against the front of the housing 7. One complete turn displaces the volume forward into the IVB. As the sweep completes a rotation, the protruding quadrant 8 stops at the neck of the tubule as it exits the housing. A complete sweep occurs in a fraction of a second.

A motor, such as a 12-ampere motor (see FIG. 1, number 12) controls the torque of the disc and is turned on by the R-wave synchronizing switch 16 and 17 (again, see FIG. 1). The torque is further regulated by a speed-reducing gear in embodiments of the disclosed technology. The gear 13 has a hundred cogs that engage with a gear of the motor shaft, such as a 6-cog gear. In an embodiment of the disclosed technology, the speed of a 12-ampere, 6,000-rpm motor is reduced to about 300 rpm as it drives the rotating disc. When the R-wave synchronizing switch disengages and the motor shuts off, the locking mechanism of the rotating disc moves a few degrees counterclockwise and clears the neck of the tubule. During this phase, the fluid in the IVB withdraws back automatically into the tubule in the housing. The R-wave synchronizing switch is discussed further with respect to FIGS. 10 through 12.

FIG. 7 shows a perspective view of a front side of a rotating disc comprising a protuding quadrant in an embodiment of the disclosed technology. FIG. 8 shows a perspective view of a back side of a rotating disc further comprising a gear engageable for turning the disc in an embodiment of the disclosed technology. FIG. 9 shows a perspective view the front side of the rotating disc as shown in FIG. 7, with a tubule extending around the disc. Note the space around the rotation disc 9 and outside of/next to the protruding quadrant 8. This is the space where the tubule 6 sits, when the rotating disc assembly is within the housing 7. As the quadrant 8 rotates about a central axis of the quadrant 8 and disc 9, liquid is pushed out of the tubule. The rotation is proximately caused by a gear shaft of a motor interacting with the beveled gear assembly 13 at the back of the disc assembly. As shown in FIG. 9, the tubule 6 is partially filled with fluid, by way of example. This fluid volume may be adjusted as described herein above, and is pushed by the quadrant 8 into the IVB 1.

FIG. 11 shows a gate mechanism within the housing in an embodiment of the disclosed technology. A complete rotation of the disc 8 is controlled by the gate mechanism. Lever 18 is located between the housing 7 and the rotating disc gear 13 (see FIG. 1). Its fulcrum 19 is the shaft 11 of the rotating disc. One end is latch 20 locks into the groove 21 of the rotating disc 8. The opposite end of the lever 18 is the motor arm 22. The motor arm 22 pushes down or pulls up the motor shaft gear 12.1 as the motor arm rotates. Immediately under the lever 18 is axle 23. One end of the axle 23 is the triangular latch pusher plate 24. This plate pushes the adjacent end of the lever against spring 25. The opposite end of the axle is a beveled gear 26 which engages with beveled gear 12.1 of the motor shaft. When the latch 20 falls into the groove 21, rotation stops. The other end of the lever is the arm that pulls up or pushes down the motor shaft. When the latch is down, the arm pulls up the motor shaft and its bevel gear away from the rotating disc-beveled gear. When the latch is up, the lever arm on the opposite end pushes down the motor shaft and its gear engages with the rotating disc gear and rotates the disc.

The seesawing of the lever is the effect of the turning axle under it. One end of the axle is a triangular plate that moves up and down the latch against a spring over it. This movement happens when the axle turns as the bevel gear at the opposite end engages with the motor shaft gear. The rotating disc can make only one effective revolution each time, because the motor shaft gear moves up and down with the lever. When it disengages with the rotating disc gear, it stops at the same time as the latch locks into the groove. In this manner, rotation of the disc and attached quadrant are precise and timed to a myocardial contraction.

Figure 12:
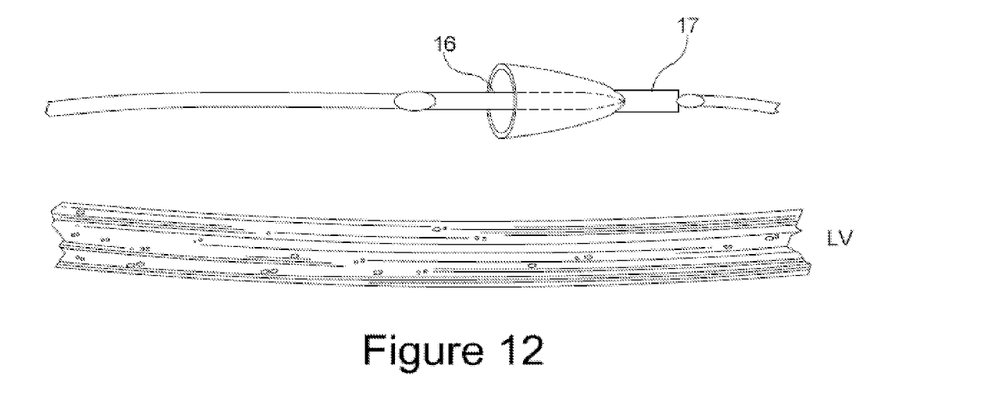
FIG. 12 shows an R-wave synchronization switch engaged with a receptacle during systole.
Figure 13:
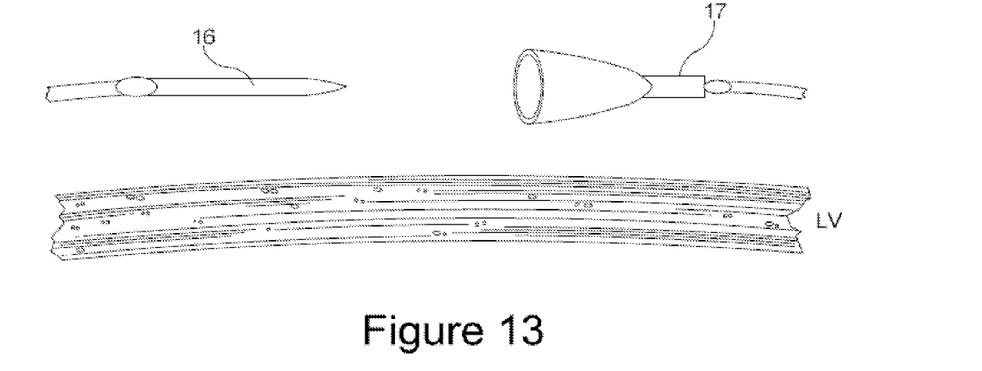
FIG. 13 shows an R-wave synchronization switch separated from a receptacle during diastole.

FIG. 12 shows an R-wave synchronization switch engaged with a receptacle during systole. FIG. 13 shows an R-wave synchronization switch separated from a receptacle during diastole. During systole (FIG. 11), shortening of muscle fibers bring the spindle activator 16 close to the receptacle 17 until the two touch each other and an electrical connection is made. The electric current then flows from the battery 14 to the generator 12, which in turn rotates the disc 9 and fills the IVB 1. During diastole (FIG. 12), the muscle fibers lengthen and the spindle activator 16 and receptacle 17 separate, ending the electrical connection and the further rotation of the disc 9, which, in embodiments of the disclosed technology, is momentarily powered from a capacitor which is electrically connected to the motor 12 to move the quadrant 8 off the portal 70, so as to allow fluid to exit back into the tubule 6 and deflate the IVB 1. This switching on-and-off repeats with every heart beat, in an embodiment of the disclosed technology, or the system/filling of the IVB may be disabled for a period of time, if medically necessary. Since IVB filling is followed by reflex emptying to a default position in the housing, every filling in systole is always followed by emptying in diastole.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the disclosed technology.

I claim:

1. An intraventricular balloon pump system, comprising:
    an intraventricular balloon;
    a housing comprising a rotating disc and a tubule, said tubule fluidly connected with said balloon;
    wherein a revolution of said rotating disc compresses said tubule and forces fluid held within said tubule to enter said balloon.

2. The intraventricular balloon pump system of claim 1, wherein said revolution is adapted to be timed with the beating of a heart.

3. The intraventricular balloon pump system of claim 2, further comprising a switch adapted to be situated on and in contact with the exterior of said heart, said switch adapted to be timed to be electrically engaged with an R-wave electrical signal of said heart.

4. The intraventricular balloon pump of claim 1, wherein said intraventricular balloon is adapted to be inserted through the apex of the heart into the left ventricle.

5. The intraventricular balloon pump system of claim 1, wherein said system is adapted to be fully implated within a person and further comprises an access port in fluid connection with said balloon and said tubule.

6. The intraventricular balloon pump system of claim 1, further comprising a grooved gear with a recess, wherein between each revolution of said rotating disc, a lever is engaged with said recess.

7. A method of ventricular assist of a heart comprising:
   filling a tubule with liquid, said tubule extending into a circular housing;
   detecting a myocardial contraction;
   upon said detecting, rotating a quadrant about a central axis of said circular housing;
   sweeping said liquid out of said circular housing into an intraventricular balloon.

8. The method of claim 7, wherein said method is repeated for a plurality of myocardial contractions.

9. The method of claim 7, wherein:
   said circular housing comprises a portal;
   said tubule exits from said portal and joins with said balloon; and
   during a portion of diastole, said quadrant rests near said portal.

10. The method of claim 7, wherein said filling is accomplished by way of a subcutaneous access port.

11. The method of claim 7, wherein when said heart beats regularly, said quadrant alternates between movement and rest.

12. The method of claim 11, wherein when said detected myocardial contraction comprises cardiac arrest, said quadrant spins continuously.

13. The method of claim 7, wherein said myocardial contraction is detected by way of an electrical switch in physical connection with an exterior portion of said heart.

14. An heart implant comprising:
   a balloon adapted to be inserted through the apex of the heart into the left ventricle;
   a circular housing further comprising a rotating quadrant therein;
   a battery powered motor connecting, by way of a gear, to said rotating quadrant;
   a tubule extending from within interior space of said circular housing to said balloon.

15. The heart implant of claim 14, further comprising an electrical switch, wherein upon detection of a myocardial contraction by way of said switch, said quadrant rotates around said circular housing and liquid within said tubule is pushed into said ventricular balloon.

16. The heart implant of claim 14, wherein said gear comprises a groove and a latch falls into said groove at each rotation of said gear.

17. The heart implant of claim 15, further comprising an access port in fluid connection with said tubule and said balloon.

18. The heart implant of claim 17, wherein a fluid volume is decreased by way of said access port when less heart assist is needed.

19. The heart implant of claim 17, wherein a maximum a fluid volume is equal to the volume of the left ventricle.

20. The heart implant of claim 14, wherein said battery is rechargeable by way of transcutaneous energy transmission.

* * * * *